United States Patent [19]
Gibbons et al.

[11] Patent Number: 5,776,905
[45] Date of Patent: Jul. 7, 1998

[54] APOPTOTIC REGRESSION OF INTIMAL VASCULAR LESIONS

[75] Inventors: Gary H. Gibbons, Palo Alto; Matthew J. Pollman, San Francisco, both of Calif.

[73] Assignee: The Board of Trustees of the Leland Stamford Junior University, Palo Alto, Calif.

[21] Appl. No.: 694,927

[22] Filed: Aug. 8, 1996

[51] Int. Cl.$^6$ .................................................. A61K 48/00
[52] U.S. Cl. .................................... 514/44; 435/69.1
[58] Field of Search ........................ 435/69.1, 810; 436/501, 63; 514/44, 2; 935/77.78

[56] References Cited

U.S. PATENT DOCUMENTS 5,583,034  12/1996  Green et al. ........................ 435/240.2

FOREIGN PATENT DOCUMENTS

WO 93/20200  10/1993  WIPO.
WO 95/00642  1/1995  WIPO.

OTHER PUBLICATIONS

Boise et al. (1993) "blc-x, a bcl-2-Related Gene That Functions as a Dominant Regulator of Apoptotic Cell Death" *Cell* 74:597-608.

Keith et al. (1995) "Inhibition of bcl-2 with Antisense Oligonucleotides Induces Apoptosis and Increases the Sensitivity of AML Blasts to Ara-C" *Leukemia* 9:131-138.

Kitada et al. (1993) "Investigations of Antisense Oligonucleotides Targeted Against bcl-2 RNAs" *Antisense Research and Development* 3:157-169.

Krajewski et al. (1994) "Immunohistochemical Analysis of in vivo Patterns of Bcl-X Expression" *Cancer Research* 54:5501-5507.

Bennett et al. (1995) "Apoptosis of Human Vascular Smooth Muscle Cells Derived from Normal Vessels and Coronary Atherosclerotic Disease" *J. Clin. Invest.* 95:2266-2274.

Miyashita et al. (1995) "Overexpression of the Bcl-2 Protein Increases the Half-life of p21$^{Bax}$" *J. Biol. Chem.* 270:26049-26052.

Cheng et al. (1996) "Bax-independent Inhibition of Apoptosis by Bcl-x$^L$" *Nature* 379:554-556.

Gibbons and Dzau (1994) "The Emerging Concept of Vascular Remodeling" *N Engl J Med* 330:1431-38.

Morishita et al. (1993) "Single Intraluminal Delivery of Antisense cdc2 Kinase and Proliferating-cell Nuclear Antigen Oligonucleotides Results in Chronic Inhibition of Neointimal Hyperplasia" *P.N.A.S.* 90:8474-8478.

Morishita et al. (1994) "Intimal Hyperplasia After Vascular Injury Is Inhibited by Antisense cdk 2 Kinase Oligonucleotides" *J Clin Invest* 93:1458-1464.

von der Leyen et al. (1995) "Gene Therapy Inhibiting Neointimal Vascular Lesion: In Vivo Transfer of Endothelial Cell Nitric Oxide Synthase Gene" *P.N.A.S.* 92:1137-1141.

Ohno et al. (1994) "Gene Therapy for Vascular Smooth Muscle Cell Proliferation After Arterial Injury" *Science* 265:781-784.

Isner et al. (1995) "Apoptosis in Human Atherosclerosis and Restenosis" *Circulation* 91:2703-2711.

(List continued on next page.)

*Primary Examiner*—Ardin H. Marschel
*Attorney, Agent, or Firm*—Pamela J. Sherwood; Bozicevic & Reed LLP

[57] ABSTRACT

Neointimal cells are shown to express high levels of an anti-apoptotic gene, bcl-x, while the medial cells of the vessel itself express only low levels. The difference in gene expression exploited to provide for selective deletion of the neointimal cells. Apoptosis is induced by administering anti-sense bcl-x oligonucleotides to the affected vessel. Apoptosis is desirable as a treatment because it does not induce inflammation, further tissue injury or reactive hyperplasia. A significant reduction in lesion size is seen after treatment.

11 Claims, 1 Drawing Sheet

OTHER PUBLICATIONS

Han et al. (1995) "Evidence for Apoptosis in Human Atherogenesis and in a Rat Vascular Injury Model" *Am. J. Path.* 147:267–277.

Wagner et al. (1993) "Antisense Gene Inhibition by Oligonucleotides Containing C-5 Propyne Pyrimidines" *Science* 260:1510–1513.

Milligan et al. (1993) "Current Concepts in Antisense Drug Design" *J. Med. Chem.* 36:1923–1937.

ic modified intimal smooth muscles. The interaction of bcl-2 or bcl-x with bax is discussed in Miyashita et al. (1995) *J. Biol. Chem.* 270:26049–26052, and Cheng et al. (1996) *Nature* 379:554–556.

APOPTOTIC REGRESSION OF INTIMAL VASCULAR LESIONS

TECHNICAL FIELD

The field of this invention is treatment of intimal lesions through the specific activation of programmed cell death.

BACKGROUND

The most common cause of morbidity and mortality in the western world is vascular disease. The fundamental pathology of vascular disease is an abnormal accumulation of cells within the subintimal space below the surface of the endothelial lining. This hypercellular intimal lesion results in a decrease in lumen size and compromised tissue perfusion. Current treatment strategies bypass the obstruction with venous conduits, or stretch the vessel to create a larger lumen by balloon angioplasty. However, neither of these therapies reduces the dimensions of the atherosclerotic or restenotic plaque. Currently, there are no drug therapies that can achieve an acute reduction in vascular lesion size. Indeed, bypass of a vessel may accelerate the progressive lesion stenosis, and interventions such as balloon angioplasty are plagued by the development of restenosis.

Apoptosis is an active, energy-dependent process, which plays an important role in a wide variety of physiological conditions ranging from loss of redundant structures during embryological development to elimination of potentially autoreactive T cells during thymic education. Cell death by apoptosis is an insidious process in which cell deletion within tissues occurs by phagocytosis by neighboring cells without evoking an inflammatory response.

The expression of certain genes has been shown to inhibit apoptosis. Among these anti-apoptotic genes are members of the bcl gene family. The proto-oncogene bcl-2 is widely expressed during mouse development and and in long-lived cells such as neurons and stem cells. bcl-x, another member of the gene family, can be alternatively spliced to produce two protein isoforms (bcl-xL and bcl-xs), of which the larger form inhibits apoptosis. bcl-x is highly expressed during development and in the brain, thymus and kidneys in adults. Cell fate appears to be determined by a balance between the expression of pro-apoptotic genes such as bax and anti-apoptotic genes such as bcl-xL. Sedlack et al. (1995) *P.N.A.S.* 92:7834 found that susceptibility to apoptosis is determined by competing dimerizations in which bax is a common partner.

Methods of specifically deleting intimal lesion cells in stenotic vessels is of great interest. Exploiting apoptotic mechanisms may provide a means of deleting such cells without further tissue injury and reactive hyperplasia.

Relevant Literature

Boise et al. (1993) *Cell* 74:597–608 and WO 95/00642 describe the molecular characterization and uses of splice variants of bcl-x. The use of anti-sense oligonucleotides having bcl-2 sequences to induce apoptosis in tumor cells is described in Keith et al. (1995) *Leukemia* 9:131–138, Kitada et al. (1993) *Antisense Research and Development* 3:157–169 and WO 93/20200. Krajewski et al. (1994) *Cancer Research* 54:5501–5507 found that bcl-x was expressed in medial smooth muscle cells. Isner et al. (1995) *Circulation* 91:2703–2711, reported bcl-2 in medial cells in human athersclerotic vessels, but not in neointimal vascular smooth muscle cells. Bennett et al. (1995) *J. Clin. Invest* 95:2266–2274, failed to detect bcl-2 in cultured phenotypi- Previous treatment strategies prevented the transition to a diseased vessel, but did not provide for treatment of pre-existing neointimal vascular lesions. Gibbons and Dzau (1994) *N Engl J Med* 330:1431–38 review vascular remodeling. Morishita et al. (1993) *P.N.A.S.* 90:8474–78 and Morishita et al. (1994) *J Clin Invest* 93:1458–64 describe the inhibition of neointimal hyperplasia with delivery of anti-sense cdk2 oligonucleotides. Gene therapy to inhibit neointimal vascular lesion by transfer of an endothelial cell nitric oxide synthase gene is described by von der Leyen et al. (1995) *P.N.A.S.* 92:1137–1141. Treatment of vascular lesions by transduction with herpes simplex thymidine kinase, and gancyclovir, is described in Ohno et al. (1994) *Science* 265:781–784.

The role of apoptosis in human atherosclerosis and restenosis is discussed in Isner et al. (1995) *Circulation* 91:2703–2711 and Han et al. (1995) *Am. J. Path.* 147:267–77.

A review of the chemistry of antisense nucleotides may be found in Wagner et al. (1993) *Science* 260:1510–1513, and in Milligan et al. (1993) *J. Med. Chem.* 36:1923–1937.

SUMMARY OF THE INVENTION

Methods are provided for the targeted deletion of intimal lesion cells in the vasculature of a mammalian patient with vascular disease. Compounds are administered that specifically block expression and/or biological activity of anti-apoptotic genes. Of particular interest are anti-sense oligonucleotides that prevent bcl-x expression. The targeted cells undergo apoptosis, thereby reducing the dimensions of an intimal lesion, e.g. an atherosclerotic or restenotic plaque. In contrast to agents that induce necrotic cell death, cell deletion by apoptosis can occur without evoking further tissue injury. The use of anti-bcl-x reagents allows the treatment to be specifically targeted to neointimal cells, while normal medial cells necessary for maintaining vessel integrity remain viable and intact.

DATABASE REFERENCES FOR NUCLEOTIDE AND AMINO ACID SEQUENCES

Figure 1A:
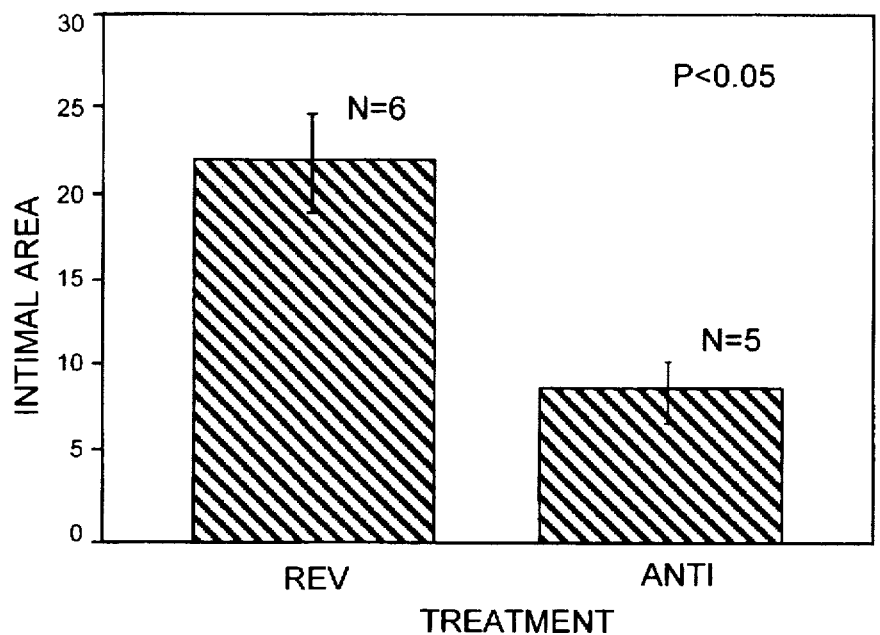
FIGS. 1A and 1B illustrate the effect of anti-sense oligonucleotides on atherosclerotic carotid arteries. The effect on intimal area is shown in FIG. 1A, and the ratio of intimal to medial cells (I/M) is shown in FIG. 1B. ODN designates oligonucleotide. REV is the control ODN transfection and ANTI is the specific antisense ODN transfection.
Figure 1B:
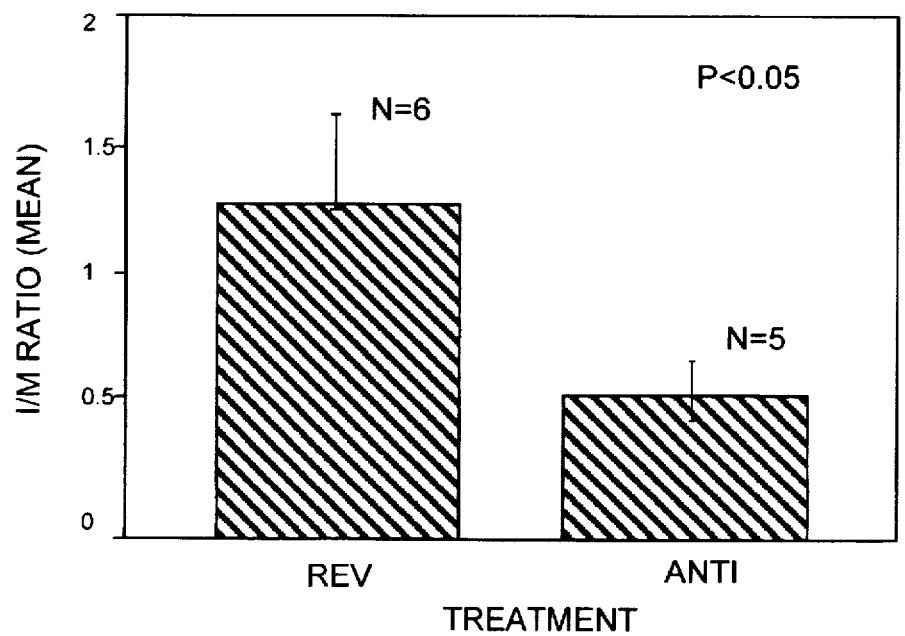

The complete mRNA sequence of mouse bcl-xL has the Genbank accession number X83574, L35049 or U10101. The complete mRNA sequence of human bcl-xs has the Genbank accession number Z23116 L20122; the bcl-xL form has the accession numbers Z23115, L20121, published by Boise et al. (1993) *Cell* 74:597–608. The gene encoding rat bcl-x gene has the Genbank accession number X82537 or U10579. The chicken bcl-x gene has the Genbank accession number Z23110 L20120

DESCRIPTION OF THE SPECIFIC EMBODIMENTS

Methods are provided to reduce the dimensions of vascular lesions resulting from neointima formation in a mammalian host. The ability to affect pre-existing lesions provides a significant therapeutic advantage over existing technologies. The neointimal cells are targeted for deletion by the administration of compounds that specifically inhibit the biological activity of anti-apoptotic genes, for example by reducing expression of the gene. Alternatively, the expression or biological activity of pro-apoptotic genes is increased. Of particular interest are anti-sense oligonucleotides that prevent bcl-x expression, thereby allowing the treatment to be specifically targeted to neointimal cells, while normal medial cells necessary for maintaining vessel integrity remain viable and intact.

Immunohistochemistry studies presented herein show that there is differential expression of bcl-x within the vessel wall, with increased expression in neointimal cells, in contrast to low expression in normal medial cells. In addition, the pro-apoptotic mediator bax is expressed throughout the vessel wall. Cell fate is apparently determined by the relative expression of the pro-apoptotic factor bax vs. the anti-apoptotic mediator bcl-x. The subject invention exploits this differential bcl-x expression to enable specific targeting to neointimal cells. By administering compounds that block the expression of the anti-apoptotic gene bcl-x, the neointimal cells are induced to undergo programmed cell death. A relative lack of bcl-2 in intimal cells apparently increases their dependence on bcl-x as the principal survival factor, therefore its inhibition causes death.

The use of the selective activation of apoptosis with the subject methods promotes the regression, as opposed to blocking development, of vascular lesions. It is a significant advantage because clinical situations generally require treatment of pre-existing conditions. A further advantage is the acute regression of lesions with the subject therapy, typically over a period of less than about four weeks, usually less than about two weeks, in contrast to the months or years that it takes to induce lesion regression with lipid lowering therapies.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like. The efficacy of the subject methods is not dependent on the mechanism of neointima formation. The host, or patient, may be from any mammalian species, e.g. primate sp., particularly humans; rodents for experimentally induced vascular lesions, including mice, rats and hamsters; rabbits; equines, bovines, canines, felines; etc. Animal models are of interest for experimental investigations, providing a model for treatment of human disease.

In a preferred embodiment, the subject therapeutic agents are antisense molecules specific for anti-apoptotic genes expressed in neointimal cells. The administered therapeutic agent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted anti-apoptotic genes, and inhibits expression of the targeted gene products. Antisense molecules inhibit gene expression by reducing the amount of mRNA available for translation, through activation of RNAse H or steric hindrance. One or a combination of antisense molecules may be administered, where a combination may comprise multiple different sequences from a single targeted gene, or sequences that complement several different genes.

A preferred target gene is bcl-x, in particular the splice variant bcl-xL. The gene sequence may be accessed through public databases as previously cited. Generally, the antisense sequence will have the same species of origin as the animal host. The bcl-x gene product is found at significantly higher levels in the neointima as compared to the normal medial cells of the vessel wall. Other anti-apoptotic members of the bcl-x gene family may also be of interest for targeting, including bcl-2, mcl-1, etc.

Combination therapies may be used to target the expression of other anti-apoptotic genes. In particular, antisense molecules specific for bcl-x may be combined with treatment to block the initiation of further hyperplasia, e.g. anti-c-myc as described in Bennett et al. (1994) *J. Clin. Invest.* 93:820–828; or anti-cdc2 or anti-cdk2, as described by Morishita et al. (1993) *P.N.A.S.* 90:8474–78; and Abe et al. (1994) *Biochem. Biophys. Res. Comm.* 198:16–24.

Antisense molecules may be produced by expression of all or a part of the target anti-apoptotic gene sequence in an appropriate vector, where the vector is introduced and expressed in the targeted neointimal cells. The transcriptional initiation will be oriented such that the antisense strand is produced as an RNA molecule. The anti-sense RNA hybridizes with the endogenous sense strand mRNA, thereby blocking expression of the targeted gene. The native transcriptional initiation region, or an exogenous transcriptional initiation region may be employed. The promoter may be introduced by recombinant methods in vitro, or as the result of homologous integration of the sequence into a chromosome. Many strong promoters that are active in muscle cells are known in the art, including the β-actin promoter, SV40 early and late promoters, human cytomegalovirus promoter, retroviral LTRs, etc.

Transcription vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in smooth muscle cells, usually for a period of at least about one day, more usually for a period of at least about several days.

Alternatively, in a preferred embodiment, the antisense molecule is a synthetic oligonucleotide. Antisense oligonucleotides will generally be from about 7 to 500, usually from about 12 to 50 nucleotides, more usually from about 20 to 35 nucleotides, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. It has been shown that the 5' region of mRNA is particularly susceptible to antisense inhibition. However, recent evidence indicates analysis of mRNA secondary structure may be important in accessibility of sites to inhibition. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Oligonucleotides may additionally comprise a targeting moiety that enhances uptake of the molecule by neointimal cells. The targeting moiety is a specific binding molecules, e.g. an antibody or fragment thereof that recognizes molecule present on the surface of smooth muscle cells, particularly hyperplastic cells. Bispecific antibodies, chimeric antibodies and single chain antibodies are known in the art. Suitably prepared non-human antibodies can be humanized in various ways. Linkage between the oligonucleotide and targeting moiety may use any conventional method, for example by disulfide, amide or thioether bonds, depending on the chemistry of the oligonucleotide backbone. Preferably the linkage will be cleaved inside the cell to liberate the oligonucleotide.

Oligonucleotides can be conjugated to hydrophobic residues, e.g. cholesterol, to protect from nucleases and to improve transport across cell membranes. Alternatively, conjugation to poly-L-lysine or other polyamines may also enhance delivery to the cell. A further modification that can be made is the addition of an intercalating component, such as acridine, capable of intercalating into the target mRNA and stabilizing the resultant hybrid. Antisense oligonucleotides may be transfected in combination with an enzyme(s) that will degrade antisense-mRNA complexes in the cell, e.g. RNase H. Any protein or enzyme that can preferentially degrade or sequester the antisense-mRNA duplex may be similarly useful.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) Nucl. Acids Res 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) Appl Biochem Biotechnol 54:43–56.

Drug screening assays may be used to identify bioactive agents that are capable of inhibiting bcl-x activity in vascular lesion cells. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified bcl-x protein may also be used for determination of three-dimensional crystal structure, which can be used for modeling intermolecular interactions, transporter function, etc.

The term "agent" as used herein describes any molecule, e.g. protein or pharmaceutical, with the capability of altering or inhibiting the physiological function of bcl-x. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment intimal lesions. Depending upon the manner of introduction, the compounds may be formulated in a variety of ways. The concentration of therapeutically active compound in the formulation may vary from about 0.1–100 wt. %.

The antisense molecules and/or other inhibitory agents are administered by contact with the vascular neointimal cells under conditions that permit entry into target cells. The molecules may be provided in solution or in any other pharmacologically suitable form for administration, such as a liposome suspension. Conveniently, the subject compositions are administered intravascularly, particularly intraarterially. The target neointimal lesion may be subject to isolation, so as to limit the flow of blood or allow for an extended period of incubation, or the active agents may be maintained in the region by virtue of having a specific affinity for target cells, or may be allowed to flow through the vasculature. The time of incubation sufficient to deliver the nucleic acids to the cells of the vasculature is usually less than about one hour, more usually less than about 30 minutes, but may be for any period of time that is both effective and practical for the in vivo isolated segment of blood vessel.

There are many delivery methods known in the art for enhancing the uptake of nucleic acids by cells. Useful delivery systems include Sendai virus-liposome delivery systems (see Rapaport and Shai (1994) *J. Biol. Chem.* 269:15124–15131), cationic liposomes, polymeric delivery gels or matrices, porous balloon catheters (as disclosed by Shi et al. (1994) *Circulation* 90:955–951; and Shi et al. (1994) *Gene Therapy* 1:408–414), intraluminal pressure (for example, see PCT/US96/06271, herein incorporated by reference), retrovirus expression vectors, and the like.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing the nucleic acids are combined in an appropriate aqueous medium, conveniently a saline medium where the total solids will be in the range of about 1–10 weight percent. After intense agitation for short periods of time, from about 5–60 sec., the tube is placed in a warm water bath, from about 25°–40° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules, particularly nucleic acids of one kbp or more. In this way oligonucleotides, plasmids, large genes, chromosomal fragments, viruses or viral segments may be introduced into cells efficiently.

The therapeutic agents are administered at a dose effective to reduce the dimensions of a pre-existing intimal lesion. Usually the lesion will be reduced in size by at least about 20% over a period of one or more weeks, more usually by at least about 50%, and may be completely regressed.

The subject therapy may be administered in combination with other molecules that induce vascular smooth muscle and monocyte-macrophage apoptosis, including molecules that prevent the dimerization of bcf-x and bax gene products; molecules that upregulate the expression of bax in neointimal cells; small molecules that interfere with bcl-x activity; inhibitors of endogenous anti-apoptotic genes not in the bcl-2 family, e.g. IAP genes; nitric oxide precursors, blockers of phosphoinositol-3-kinase, inhibitors of cell cycle progression (e.g. aphidocolin), etc. Local delivery of a pro-apoptotic drug (e.g. a nitric oxide releasing agent) NO-donor agents (sodium nitroprusside and sodium N-acetyl penicillamine [0.1–500 uM]) may be combined with delivery of antisense molecules.

The following examples are offered by way of illustration and not by way of limitation.

EXPERIMENTAL

Example 1

Expression of bcl-x in neointima of Athersclerotic Lesions Materials and Methods 4 wk Rabbit atheroma tissue: Rabbit polyclonal antibodies specific for a peptide sequence with 100% homology between human and mouse were obtained from Santa Cruz Biotechnology, Santa Cruz, Cailf. The antibodies were biotinylated with a biotinylation kit (Pierce Corp) in accordance with the manufacturer's instructions.

Rabbit purified IgG (Sigma, St Louis Mo.) biotinylated in same manner as the specific antibody was used as a control. In an additional control, specific antibody staining was blocked by pre-absorption of antibody with peptide. Preabsorption by peptide (Santa Cruz Biotechnology) added a 10× excess by wt of peptide to antibody for 45 min at room temperature prior to application of the primary antibody.

Immunochemistry protocol: acetone-fixed 6 μm cryosections from rabbit atheroma tissue were treated with peroxidase block (Dako Corp, Carpinteria, Cailf.), and pre-blocked for 60 minutes at room temperature (RT) with Tris-buffered saline containing 0.5M sodium chloride and 0.1% Tween-20 (TBS-T) with 5% non-fat dried milk and 5% normal rabbit serum. Samples were then incubated with the primary antibody (1:10 dilution) for 60 min RT, rinsed and incubated with streptavidin peroxidase (Dako Corp) for 30 min RT. After rinsing in TBS-T, samples were incubated with AEC for 5 min RT, rinsed, mounted and photographed at 100× under light microscopy.

Human atheroma: a sample of diseased left anterior descending artery was taken from a 57 year old male who underwent heart transplantation for ischemic cardiomyopathy. A rabbit polyclonal anti-bcl-x antibody generated against a 250 aa fragment of human bcl-x protein and exhibiting a broad species cross reactivity (Transduction Laboratories, Lexington, Ky.) was used for immunohistochemistry. Purified rabbit IgG (Sigma) was used as a control antibody.

Immunohistochemistry protocol: acetone-fixed 6 μm cryosections were treated with peroxidase block for 5 min RT (Dako Corp) and pre-blocked for 60 min RT with TBS-T containing 10% goat serum and 2% bovine serum albumin. Samples were incubated with primary antibody (25 μg/ml) in blocking buffer for 60 min RT, rinsed and incubated 60 min RT with secondary goat-anti rabbit antibody (Vector Laboratories, Burlingame, Cailf.), followed by a rinse and incubation 60 min RT with streptavidin peroxidase (Dako Corp). After rinsing, samples were incubated with AEC for 5 min RT, rinsed, mounted and photographed at 100× under light microscopy.

Results

Using an anti-bcl-x antibody and immunohistochemistry, high protein expression levels of an anti-apoptotic gene, bcl-x, were observed in the neointima of rabbit and human atherosclerotic lesions as compared to relatively low levels in the normal medial layer.

Example 2

Down-Regulation of bcl-x in Neointima

Antisense oligonucleotides complementary to either bcl-x mRNA or a control sequence were administered to the vasculature of rabbits having two different neointimal hyperplasia models. The specific antisense oligonucleotides induced apoptosis in the neointimal cells, while leaving the medial cells substantially unaffected.

Materials and Methods

Antisense Oligonucleotides: A DNA oligonucleotide encoding a sequence complementary to the coding region three bases upstream of the translation initiation codon site for the bcl-x gene and extending 3' downstream for a total of 18 bases with the sequence [SEQ ID NO:1] 5'-GTTGCTCTGAGACATTTT-3' was synthesized with a phosphorothioate backbone. As a control oligonucleotide, a sequence of identical length and composition but in the reverse order [SEQ ID NO:2] 5'-TTTTACAGAGTCTCGTTG-3 was synthesized. An additional missense control sequence, containing a 4 bp mismatch as compared to antisense sequence was also used [SEQ ID NO:3] 5'-GTTGCTGTCACAGATTTT-3'. The oligonucleotides were purified by HPLC.

Animal Models: 2–3 kg male New Zealand White rabbits were utilized to form two model groups.

(1) Neointimal hyperplasia model of restenosis: the right carotid artery was subjected to a standard catheter balloon injury and a neointimal cellular accumulation was allowed to develop over a four week period while being fed normal chow. This is a well established model that results in a neointimal lesion primarily composed of phenotypically modified vascular smooth muscle cells (see, for example, Freyschuss et al. (1993) *J. Clin. Invest.* 91:1282).

(2) Neointimal hyperplasia model of atherosclerosis: rabbits were prefed a 1% cholesterol diet for two weeks prior to the standard catheter balloon injury and continued on a 1% cholesterol diet for the four week period of neointimal cellular accumulation post-balloon injury. This well established model results in a mixed neointimal lesion composed of both phenotypically modified vascular smooth muscle cells and foamy lipid-laden macrophages reminiscent of an early atheromatous plaque.

Pressure-Mediated Delivery of Antisense Oligonucleotide: Four weeks post-balloon injury, the diseased right carotid artery was surgically exposed and a 40 micromolar solution in phosphate-buffered saline of either the antisense or control oligonucleotide was introduced intraluminally via catheter through the internal carotid artery. An intraluminal pressure of 1 atmosphere above ambient pressure was maintained for 10 minutes while the outer vessel was sheathed in a cuff to prevent distension-related vessel injury. The efficacy and extent of oligonucleotide delivery using this approach was previously verified with fluorescently-labeled oligonucleotides and indicated high-efficiency delivery throughout the vessel, including the entire neointima and media.

Assessment of Apoptosis: 24 hours post-transfection, animals were sacrificed and the transfected vessels were fixed in formalin and stained with the DNA-binding dye Hoechst 33342. UV microscopy was used to examine vessels for the presence of cells displaying a condensed and coalesced pattern of nuclear staining, which is recognized as indicative of cells undergoing apoptosis, as verified by other techniques including electron microscopy, DNA laddering, flow cytometry and in situ end-labeling of nicked DNA.

(1) Nuclear chromatin morphology: The luminal surface of the vessels were viewed en-face under 400× UV microscopy after staining with 5 μg/ml H33342 in PBS for 60 min RT. 1000 cells in random fields were analyzed in a blinded fashion for normal vs condensed and coalesced (apoptotic) nuclear chromatin morphology. Results are expressed as the percent of apoptotic nuclei over total nuclei analyzed.

2) DNA Laddering: the neointima of vessels 24 hours after treatment with antisense vs control oligos was selectively removed by dissecting along a plane of dissection above the internal elastic lamina with micro-scissors and forceps under a 10× dissecting microscope. The tissue was finely minced and incubated at 55° C. for 3 hrs in a lysis buffer consisting of 100 mM NaCl, 10 mM Tris-Cl pH 8.0, 25 mM EDTA pH 8.0, 0.5% SDS and fresh 0.15 mg/ml proteinase K. The DNA was extracted twice with equal volumes of phenol:chloroform:isoamyl alcohol and precipitated in the presence of 3M ammonium acetate, 10 mM magnesium chloride and 2.5 volumes of ethanol at −20° C. overnight. After RNase treatment (12.5 μg/ml, 1 hr 37° C.), DNA samples were phenol extracted and ethanol precipitated as above. Care was taken in the handling of cells and extracted DNA to minimize nicking or shearing of DNA that generates random length 3'-OH-ends, which may compete with oligonucleosomal length fragments in the end-labeling reaction. Extracted and purified DNA was 3'-end labeled and size fractionated by agarose gel electrophoresis for autoradiography. This technique allows for increased sensitivity in determining DNA fragmentation in relatively small quantities of DNA.

Reagents for end-labeling were obtained from Boehringer-Mannheim (Indianapolis, Ind.) and include terminal deoxynucleotide transferase enzyme, 5× concentrated reaction buffer (1M potassium cacodylate, 0.125M Tris-Cl, 1.25 mg/ml bovine serum albumin; pH 6.6) and cobalt chloride (25 mM). Radio-labeled dideoxy-nucleotide, [α$^{32}$P]-ddATP; 3,000 Ci/mmol, was obtained from Amersham (Arlington Heights, Ill.). Purified DNA (1 µg) was incubated for 1 hr at 37° C. in the presence of 50 µCi [α$^{32}$P]-ddATP, 25 U terminal deoxynucleotide transferase, 1× reaction buffer and cobalt chloride. The reaction was terminated by the addition of 25 mM EDTA (pH 8.0). Unincorporated radionucleotide was separated from labeled DNA by two successive precipitations with 0.2× volumes 10M ammonium acetate and 3×volume of 100% ethanol in the presence of 50 µg tRNA. One half of the labeled sample was loaded on a 2% agarose gel and separated by electrophoresis for 3 hrs at 50 volts in 1×TAE buffer. The gel was subsequently dried and exposed to Kodak X-Omat film for 2 hrs at −70° C.

Assessment of Lesion Size and Documentation of Regression: One week post-transfection, animals were sacrificed and the transfected vessels were pressure-fixed in glutaraldehyde and sequentially sectioned every 100 microns. Tissue sections were subjected to computer-assisted morphometric analysis by an observer blinded to the treatment groups.

Results

Inhibition of bcl-x expression in vivo: vessels were transfected with either anti-bcl-x antisense oligonucleotides or control oligonucleotides (missense sequence or 3'-5' reverse sequence) and compared to untreated vessels. Protein expression of bcl-x was determined by Western blot. The specific antisense oligonucleotide treatment resulted in a marked decrease in bcl-x levels 18 hours after transfection, compared to the controls. In blots reprobed for the expression of vimentin (as a normal control), there were minimal differences in protein expression. Vimentin is a cellular protein expressed at similar quantities in extracts from vessels transfected with the anti-bcl-x antisense oligonucleotides as compared to control vessels. Therefore, the antisense oligonucleotides selectively inhibited bcl-x expression in a sequence specific manner.

Induction of Apoptosis: Numerous apoptotic cells were observed throughout the neointima that had been transfected with the antisense oligonucleotide. The frequency of apoptotic cells in the antisense oligonucleotide treated vessels was several-fold greater than that observed in the control oligonucleotide transfected vessels from animals in both model groups (restenosis and atherosclerosis). This massive apoptosis was confined to the neointima, no apoptosis was observed in the media of transfected vessels. Diseased vessels from untransfected animals exhibited the same low level of apoptosis observed in the control oligonucleotide treated group. Transfection of anti-bcl-x antisense oligonucleotides into the media of normal vessels failed to induce apoptosis. The analysis of DNA fragmentation by gel electrophoresis provides biochemical confirmation that the increase in cell death involves apoptosis.

Lesion Regression: as determined by morphometric analysis, atherosclerotic vessels from the antisense-treated animals exhibited a significant reduction in lesion size as compared to control-transfected animals. Intimal:medial ratios were reduced by 60% and intimal areas were reduced by 50% in the antisense vs control-transfected animals.

It is evident from the above results that the subject invention provides for a means of reducing the dimensions of pre-established neointimal lesions. Immunohistochemistry studies show that there is differential expression of the anti-apoptotic gene bcl-x within the vessel wall, with increased expression in neointimal cells, in contrast to low expression in normal medial cells. By exploiting apoptotic mechanisms, hyperplastic cells in vascular regions are deleted without reactive hyperplasia and further tissue injury to the walls of the vessel. Antisense oligonucleotides are administered to the injured vessel, resulting in activation of apoptosis in the vascular lesion. The use of the selective activation of apoptosis to promote the regression of lesions is a significant advantage over previous therapies that are only effective prior to the development of the neointimal lesion.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing the dimensions of a neointimal vascular lesion in a patient, the method comprising:

administering an effective amount of a synthetic antisense oligonucleotide that specifically blocks expression of bcl-x;

wherein apoptosis is induced in said neointimal cells, thereby reducing the dimensions of said neointimal vascular lesion.

2. A method according to claim 1, wherein said synthetic antisense oligonucleotide comprises a phosphorothioate backbone.

3. A method according to claim 1, wherein said antisense oligonucleotide is administered by pressure-mediated delivery.

4. A method according to claim 1, wherein said antisense oligonucleotide is administered by liposome delivery.

5. A method according to claim 1, wherein said neointimal hyperplasia is an athersclerotic lesion.

6. A method according to claim 1, wherein said synthetic antisense oligonucleotide is complementary to the region of the translation initiation codon of bcl-x.

7. A method of reducing the dimensions of a neointimal vascular lesion in a patient, the method comprising:

administering an effective amount of a synthetic antisense oligonucleotide that (a) specifically blocks expression of bcl-x; and (b) is complementary to the region of the translation initiation codon of bcl-x;

wherein apoptosis is induced in said neointimal cells, thereby reducing the dimensions of said neointimal vascular lesion.

8. A method according to claim 7, wherein said synthetic antisense oligonucleotide comprises a phosphorothioate backbone.

9. A method according to claim 7, wherein said antisense oligonucleotide is administered by pressure-mediated delivery.

10. A method according to claim 7, wherein said antisense oligonucleotide is administered by liposome delivery.

11. A method according to claim 7, wherein said neointimal hyperplasia is an athersclerotic lesion.

\* \* \* \* \*

UNITED STATES PATENT AND TRADEMARK OFFICE
CERTIFICATE OF CORRECTION

PATENT NO.   : 5,776,905
DATED        : July 7, 1998
INVENTOR(S)  : Gary H. Gibbons, et al.

It is certified that error appears in the above-identified patent and that said Letters Patent is hereby corrected as shown below:

On the title page:

Please Correct Under Assignee to Read As Follows:

[73] Assignee: The Board Of Trustees Of The Leland Stanford Junior University, Palo Alto, Calif.

Signed and Sealed this

Twenty-third Day of February, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:1:

GTTGCTCTGA GACATTTT                                                  18

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:2:

TTTTACAGAG TCTCGTTG        18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:3:

GTTGCTGTCA CAGATTTT        18